US 9,649,231 B1

(12) United States Patent
Tilker

(10) Patent No.: US 9,649,231 B1
(45) Date of Patent: May 16, 2017

(54) MULTIPLE-LAYER UNDERGARMENT FOR TOILET TRAINING

(76) Inventor: Lynn Tilker, San Diego, CA (US)

(*) Notice: Subject to any disclaimer, the term of this patent is extended or adjusted under 35 U.S.C. 154(b) by 856 days.

(21) Appl. No.: 13/608,384

(22) Filed: Sep. 10, 2012

Related U.S. Application Data

(63) Continuation-in-part of application No. 13/241,749, filed on Sep. 23, 2011, now abandoned.

(60) Provisional application No. 61/394,464, filed on Oct. 19, 2010.

(51) Int. Cl.
*A61F 13/15* (2006.01)
*A61F 13/505* (2006.01)
*A61F 13/49* (2006.01)
*A61F 13/45* (2006.01)

(52) U.S. Cl.
CPC ...... *A61F 13/505* (2013.01); *A61F 13/49001* (2013.01); *A61F 13/49003* (2013.01); *A61F 13/49004* (2013.01); *A61F 13/49006* (2013.01); *A61F 2013/4587* (2013.01); *A61F 2013/5055* (2013.01)

(58) Field of Classification Search
CPC .............. A61F 13/505; A61F 13/49006; A61F 13/49003; A61F 13/49004; A61F 13/49001; A61F 2013/5055; A61F 2013/4587
USPC ............. 604/385.14, 385.11, 385.13, 385.15
See application file for complete search history.

(56) References Cited

U.S. PATENT DOCUMENTS

| | | | |
|---|---|---|---|
| 2,839,058 A | 6/1958 | Biever | |
| 5,405,342 A | 4/1995 | Roessler et al. | |
| 5,702,376 A | 12/1997 | Glaug et al. | |
| 5,797,892 A | 8/1998 | Glaug et al. | |
| 6,727,404 B2 | 4/2004 | Ruman et al. | |
| 6,793,650 B2 | 9/2004 | Weber | |
| 7,135,013 B2 | 11/2006 | Olson et al. | |
| 7,615,675 B2 | 11/2009 | Roe et al. | |
| 7,705,194 B2 | 4/2010 | Underhill et al. | |

*Primary Examiner* — Jacqueline Stephens
(74) *Attorney, Agent, or Firm* — Orrick, Herrington & Sutcliffe LLP

(57) ABSTRACT

A multiple-layer undergarment to aid toilet training that provides a child with a sensation of wetness, but protects the child's outer garments from being saturated. The undergarment has an inner fabric layer that retains wetness to produce the uncomfortable sensation for the child after urinating in the undergarment. The undergarment has an absorbent layer sandwiched between two fabric layers that absorbs the excess wetness, the absorbent layer selectively having a barrier layer preventing urine from soaking through to the child's outer garments. In one embodiment, the undergarment has a channel extending from a front waistband, through a crotch to a back waistband for inserting an absorbent panel. In another embodiment, the undergarment has an absorbent insert attached by a plurality of adhesive strips between two fabric underwear. In one embodiment, the undergarment has a channel for inserting an absorbent panel attached by at least one adhesive strip.

14 Claims, 7 Drawing Sheets

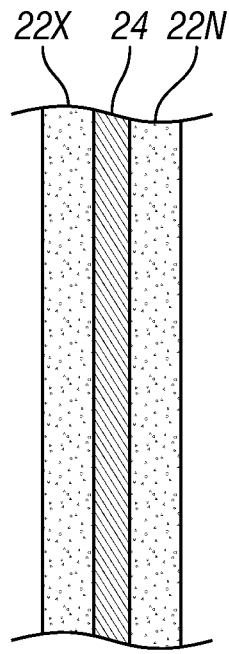
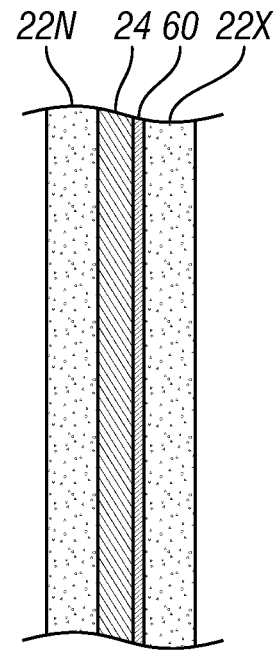
FIG. 2A  FIG. 2B
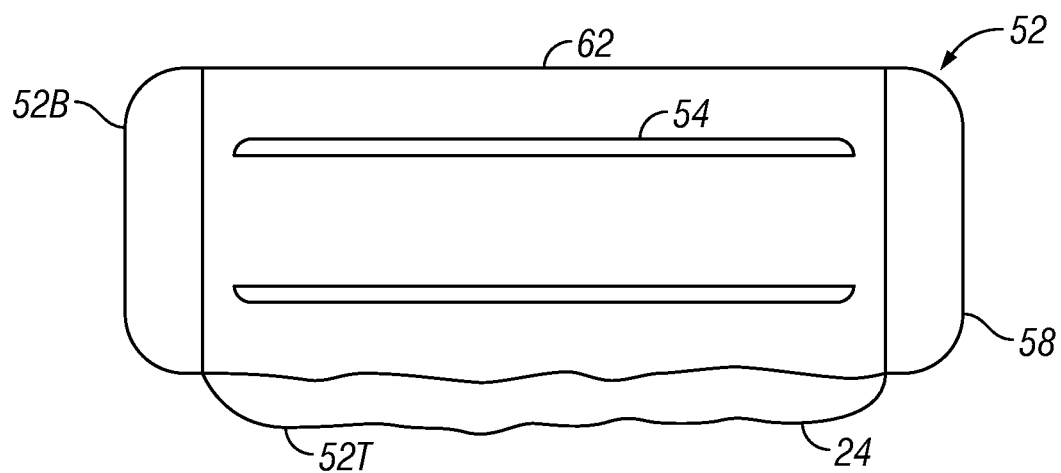
FIG. 3

MULTIPLE-LAYER UNDERGARMENT FOR TOILET TRAINING

CROSS-REFERENCE TO RELATED APPLICATIONS

This application is a continuation-in-part of the nonprovisional utility application, Ser. No. 13/241,749 filed in the United States Patent Office on Sep. 23, 2011, which claims the priority of the provisional patent application, Ser. No. 61/394,464 filed in the United States Patent Office on Oct. 19, 2010 thereof, and are expressly incorporated herein by reference in its entirety.

TECHNICAL FIELD

The invention relates generally to a multiple-layer undergarment for toilet training. More particularly, the invention relates to multiple-layer undergarment to aid toilet training that provides the child with a sensation of wetness, but protects the child's outer garments from being saturated with urine or soiled by feces.

BACKGROUND

Parents are eager to teach their young children how to use the toilet to abandon diapers with all of their inconveniences. Training pants are useful in toilet training children and cloth training pants are widely available. Typically, these cloth undergarments that are currently available are similar to washable, cloth underwear in how they are put on and worn, yet also provide an absorbent function like diapers to draw and retain urine, while still providing a feeling of wetness to the child. Unlike diapers, the child can independently remove the training pants and replace the undergarment when finished with toileting. Training pants provide a child with an undergarment that eases the transition from diapers to cloth underwear as they become more confident in their ability to use the toilet independently. However, unlike diapers, cloth training pants do not protect the child's outer clothing.

Parents may choose to ease the transition to cloth underwear by using disposable training pants. While these protect the child's outer clothing from soiling, they do not provide the feeling of wetness that cloth training pants provide.

In order to learn to use the toilet independently, a child must first recognize the connection between the urge to urinate and urination occurring so that this bodily function may be controlled. Similarly, the child must associate the urge to defecate and defecation. This is the biggest hurdle in the training process as these acts may often occur during an activity that distracts the child sufficiently so that the child does not notice that he or she has had an "accident." Also, a child's ability to recognize when he or she has urinated may be hampered by disposable absorbent undergarments that quickly draw and retain urine away from the wearer's skin after the child has wet without providing a signal to the child.

Many believe that a child must feel wetness on the skin to signal that he or she has had an accident and to associate the feeling of the urge to urinate with urinating. The feeling of wetness promotes timely use of the toilet to avoid the uncomfortable damp, soggy sensation that follows.

Parents can choose between the traditional fabric training pants and disposable super-absorbent "pull-ups". The traditional fabric training pants provide that feeling of wetness, but provide no protection to the outer garments against wetness and soiling. When beginning the toilet training process, children have many accidents, soiling and wetting the training pants and outer garments several times a day. If the parent chooses to use the traditional fabric style that provides the wetness feeling, the result is a significant increase in laundry, because the soiled and wet outer garments as well as the training pants must be changed frequently and laundered.

Disposable training pants quickly pull the wetness away from the skin without providing the child with a sensation of wetness. While these prevent soiling and wetting outer garments, they may inhibit the training process. Others have attempted to provide toilet training aids that alert a child that urination has occurred, without the feeling of wetness, particularly when disposable super-absorbent pants are used. For example, it has been proposed to have pads inserted or incorporated into the disposable toilet training underwear that include a temperature change indicator, a dimensional change indicator or an effervescence gas emission when contacted with urine to alert the child that he or she has urinated. Also absorbent articles have been proposed that have an initial wet feel to alert the child that urination has occurred. This initial wetness lasts only a short time after which the surface moisture value drops to a lower level resulting in a drier feeling to the child and eliminates the uncomfortable soggy, wet sensation.

While these proposed indicators in disposable pants alert the child, they do not provide the wetness sensation and the uncomfortable feeling that gives biofeedback to the child. The alternative to disposables leaves the prospect of mountains of extra laundry. There continues to be a need for simple, effective articles that alert children that urination has occurred and also protects outer garments from staining and wetness.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a multiple-layer undergarment to aid toilet training a young child that allows the child to feel a sensation of wetness after wetting the undergarment. Accordingly, an aspect of an example embodiment in the present disclosure provides a multiple-layer undergarment having an inner fabric layer that retains wetness to produce a sensation of wetness for the child after urinating in the undergarment.

A further aspect of an example embodiment in the present disclosure is to provide a multiple-layer undergarment to aid toilet training a young child that prevents wetness soaking through to outer garments. Accordingly, an aspect of an example embodiment in the present disclosure provides a multiple-layer undergarment having an absorbent layer that absorbs the excess wetness, preventing urine from soaking through to outer garments.

Another aspect of an example embodiment in the present disclosure is to provide a multiple-layer undergarment to aid toilet training a young child that maintains the absorbent layer and provides extra protection, preventing urine from soaking through to outer garments. Accordingly, an aspect of an example embodiment in the present disclosure provides a multiple-layer undergarment having an outer fabric layer that maintains the absorbent layer and provides extra protection, preventing urine from soaking through to outer garments.

Yet a further aspect of an example embodiment in the present disclosure is to provide a multiple-layer undergarment to aid toilet training a young child that has a disposable absorbent layer between two fabric layers. Accordingly, an aspect of an example embodiment in the present disclosure provides a multiple-layer undergarment having a channel to insert a disposable absorbent layer between two fabric layers.

An aspect of an example embodiment in the present disclosure is to provide a multiple-layer undergarment to aid toilet training a young child that has a disposable absorbent layer that attaches to a fabric underwear, but maintains a fabric layer next to the child. Accordingly, an aspect of an example embodiment in the present disclosure provides a multiple-layer undergarment having a first fabric underwear joined to second fabric underwear at a pair of legbands and optionally at a waistband and a disposable absorbent insert that is attached between the two fabric underwear, maintaining a fabric layer next to the child.

The present disclosure describes a multiple-layer undergarment to aid toilet training that provides a child with a sensation of wetness, but protects the child's outer garments from being saturated. The undergarment has an inner fabric layer that retains wetness to produce the uncomfortable sensation for the child after urinating in the undergarment. The undergarment has an absorbent layer sandwiched between two fabric layers that absorbs the excess wetness, the absorbent layer selectively having a barrier layer preventing urine from soaking through to the child's outer garments. In one embodiment, the undergarment has a channel extending from a front waistband, through a crotch to a back waistband for inserting an absorbent panel. In another embodiment, the undergarment has an absorbent insert attached by a plurality of adhesive strips between two fabric underwear. In one embodiment, the undergarment has a channel for inserting an absorbent panel attached by at least one adhesive strip.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

FIG. 2A is a cross-section view of the layers of the multiple-layer undergarment showing an absorbent layer sandwiched between a pair of fabric layers.

FIG. 2B is a cross-section view of the layers of the multiple-layer undergarment, similar to FIG. 2A, showing the absorbent layer with a barrier layer sandwiched between the pair of fabric layers.

FIG. 3 is a diagrammatic perspective view of an absorbent insert for placing between a pair of fabric training underwear that has been joined together.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
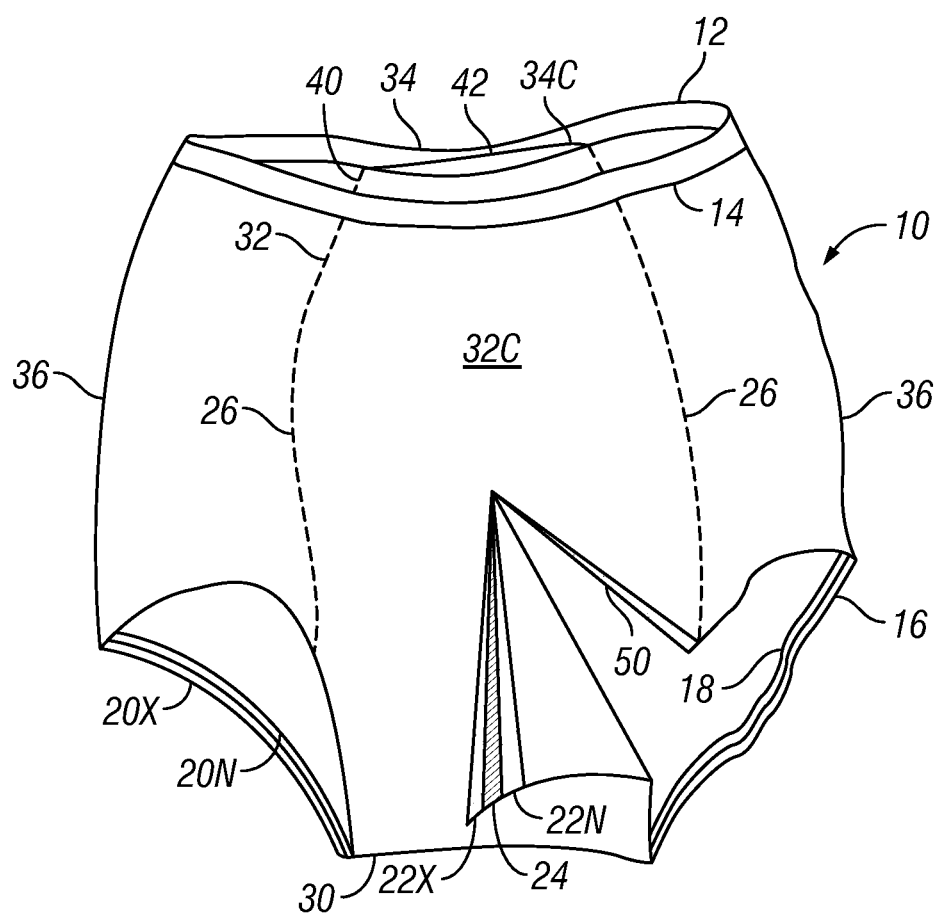
FIG. 1 is a diagrammatic perspective view of multiple-layer underwear with a section cut open to show a plurality of layers.

FIG. 1 illustrates a multiple-layer undergarment 10 for use in toilet training a young child. In one embodiment, the multiple-layer undergarment has a plurality of layers joined together, having an outer fabric layer 22X, an inner fabric layer 22N, and an absorbent layer 24 between the outer fabric layer 22X and the inner fabric layer 22N. The inner fabric layer 22N retains sufficient wetness and remains wet after the child urinates, providing the child with the sensation of wetness. The wetness on the skin signals the child that an accident has occurred and to associate the feeling of the urge to urinate with urinating and the soggy wet feeling that follows. The feeling of wetness promotes timely use of the toilet to avoid the uncomfortable feeling. The absorbent material 24 will prevent the wetness from reaching the outer clothing. The outer layer 22X provides the shape and feel of an undergarment and maintain for the absorbent layer 24.

The multiple-layer undergarment 10 has an opening 12 for the waist with a peripheral waistband 14, a pair of leg openings 16 each with peripheral legbands 18, a crotch 30 between the leg openings 16, a front 32 and a back, each extending from the crotch 30 to the waistband 14, a pair of sides 36, extending from the legbands 18 to the waistband 14, connecting the front and the back. The front 32 and the back 34 have each have a center portion 32C, 34C between the pair of sides 36.

FIG. 1 shows a cutaway section showing the multiple layers of the undergarment. In the embodiment shown, the absorbent layer 24 is a panel 50 sandwiched between the fabric layers 22X, 22N. The absorbent layer panel 50 extends from the waistband 14 in the front 32 down the center 32C of the front to the crotch 30 and around to the back 34 extending up the center 34C of the back to the waistband 14. The panel 50 is sandwiched between a pair of fabric underwear, a first outer underwear 20X and a second inner underwear 20N. The pair of underwear 20X, 20N and the absorbent panel 50 are joined at the waistband 14 and at the legbands 18 with a pair of seams 26 extending from the waistband 14 in the front 32 to the waistband 14 in the back 34 where the center portions of the front 32C and the back 32 meet the sides 36, one seam 26 on each side 36, to keep the absorbent panel 50 in place. In a further embodiment, there is at least one opening 42 at the waistband 14 where the two fabric layers 20 join in the center 32C of the front, in the center of the back 34C or both, creating a channel 40 for the absorbent panel 50. The panel 50 is inserted in the channel 40 and then removed for washing the undergarment. The absorbent panel 50 can be disposable.

In yet a further embodiment, the absorbent layer 24 is optionally the same size and shape as the inner fabric layer 20N and outer fabric layer 20X and is congruent with the two layers, such that there are substantially three sets of underwear joined together at the waistband 14 and legbands 18, a first fabric underwear 20N forming the inner fabric layer 22N, and a second fabric underwear 20X forming the outer fabric layer 22X and a third underwear of absorbent material 24 sandwiched between the first and the second underwear. The fabric underwear with the absorbent underwear is machine washable and machine dryable. In another embodiment, the fabric underwear and the absorbent underwear are disposable.

FIG. 1 shows a cutaway section demonstrating the multiple layers of the multiple-layer undergarment 10, showing the inner fabric layer 22N, the absorbent layer 24, and the outer fabric layer 22X. The cutaway section is shown in cross section in the FIG. 2A, showing the absorbent layer 24 sandwiched between the fabric layers 22X, 22N.

Figure 4:
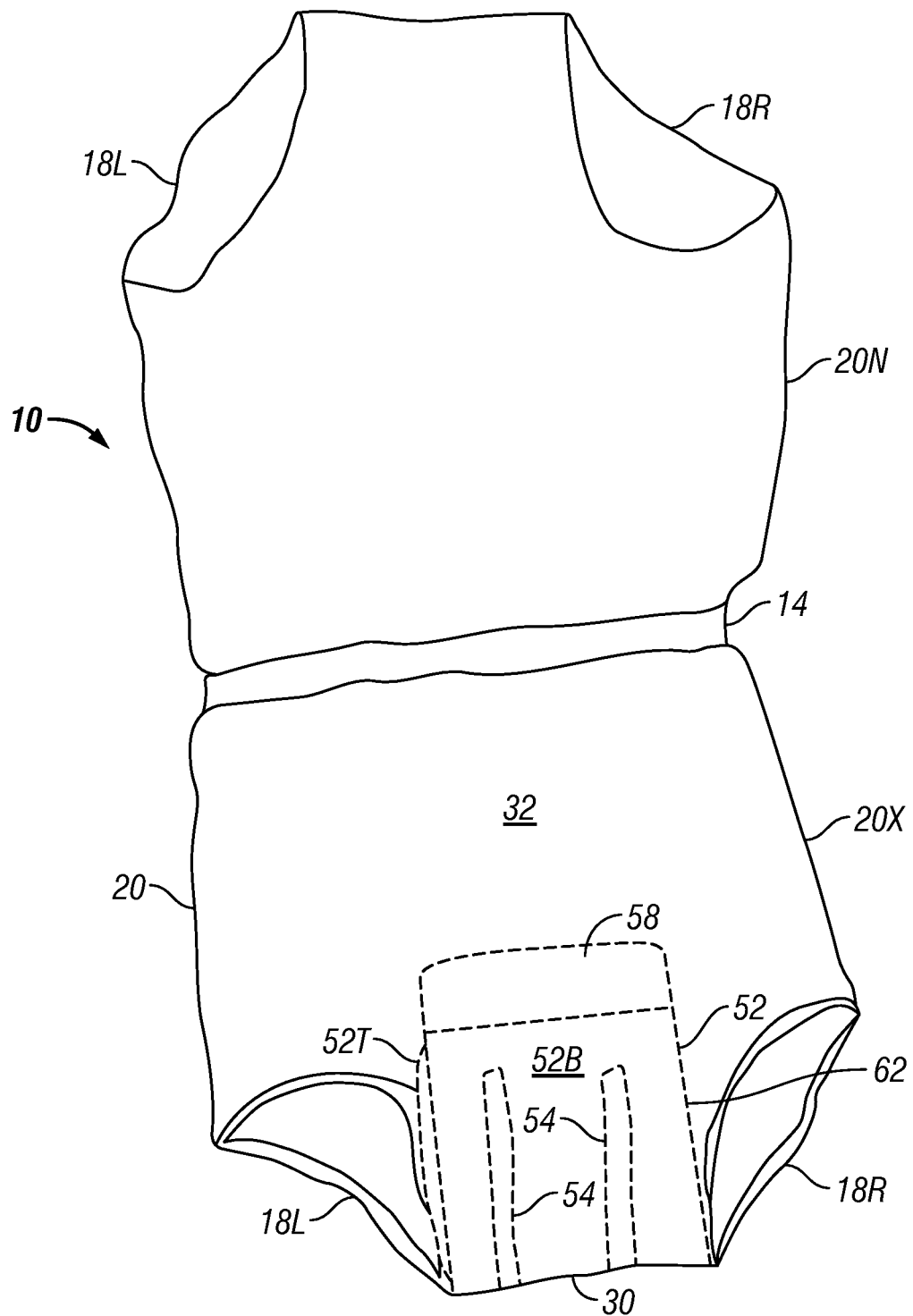
FIG. 4 is a diagrammatic perspective view of a pair of fabric underwear that has been joined at a waistband with the absorbent insert in an interstice.

In another embodiment, shown in FIG. 4, two fabric underwear 20 are joined together at the waistbands 14 forming an interstice when the waistband 14 is folding, one fabric underwear nesting inside the other. An absorbent insert panel 52, having a bottom side 52B and a top side 52T, is placed on the crotch 30 on the inside of the outer underwear 20X, extending up the front and back centers 32C, 34C. The absorbent insert panel 52 is shown in FIG. 3. The bottom side has a support sheet 62 and the top side has the absorbent material 24. The support sheet 62 optionally is longer than the absorbent material 24 and extends beyond the absorbent material 24 to create at least one tab 58 for grasping when removing the insert. The insert has a plurality of adhesive strips 54 on the bottom side 52B opposite the absorbent material to attach the insert 52 to the inside of the outer underwear 20X. The pair of the legbands of the fabric underwear optionally attaching, a left legband 18L of the outer underwear attaches to a left legband 18L of the inner underwear and a right legband 18R of the outer underwear attaches to a right legband 18R of the inner underwear.

Referring to FIG. 4, the insert 52 can be varied, depending on the gender of the child, having a longer insert for a boy or by placing the insert 52 more toward the waistband 14 in the front 32. In one embodiment, the support sheet 62 on the bottom side 52B can have a barrier layer that is a thin sheet of breathable polyethylene or similar plastic film on the bottom side. FIG. 2B shows a cross-section of the crotch of the multiple-layer undergarment with the insert 52 having the barrier layer 60 in place. The absorbent layer 24 is sandwiched between the outer fabric layer 22X and the inner fabric layer 22N, and the barrier layer 60 is sandwiched between the outer fabric layer 22X and the absorbent layer 22N.

Figure 5:
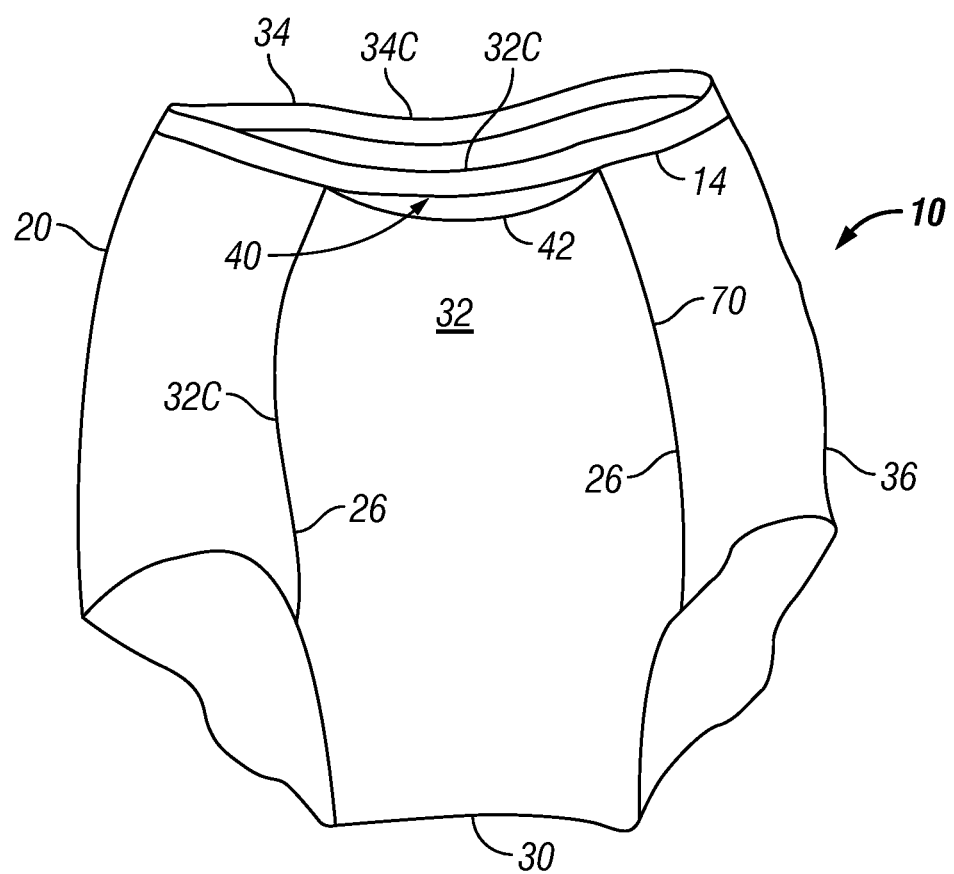
FIG. 5 is a diagrammatic perspective view of fabric underwear with a fabric panel forming a channel for inserting an absorbent panel.

FIG. 5 shows yet another embodiment of the invention. One fabric underwear 20 with one complete fabric layer is shown. An additional fabric panel 70 is attached from the waistband 14 in the front center 32C, extending through the crotch 30, and further extending to the waistband 14 in the back center 34C. A pair of seams 26 joining the fabric panel 70 to the underwear 20 extend from the waistband 14 in the front 32 to the waistband 14 in the back 34 where the center portions 32C, 34C of the front 32 and the back 32 meet the sides 36, one seam on each side. There is at least one opening 42 at the waistband 14 where the fabric panel 70 joins the fabric underwear 20 in the center 32F of the front 32, in the center 34C of the back 34 or both, creating a channel 40 for the absorbent panel (which is not shown). The fabric panel 70 may be attached to outside or the inside of the fabric underwear 20. The absorbent panel is inserted in the channel 40 and then removed for washing the undergarment. The absorbent panel can be disposable.

If the fabric panel 70 is on the inside of the underwear 20, the absorbent panel is inserted, creating a sandwich of the inner fabric panel 70, the outer fabric underwear 20 and the absorbent panel between the inner fabric panel 70 and the outer fabric underwear 20. The absorbent panel has a pair of long sides the length of the panel. Optionally, the absorbent panel may have a barrier layer that is a thin sheet of breathable polyethylene or similar plastic film on the long side. The barrier layer is placed in the channel 40 facing the outer fabric underwear 20.

If the fabric panel 70 is on the outside of the underwear 20, the absorbent panel is inserted, creating a sandwich of the inner fabric underwear 20, the outer fabric panel 70 and the absorbent panel between the inner fabric underwear 20 and the outer fabric panel 70. The barrier layer is placed in the channel facing the outer fabric panel.

To use the multiple-layer undergarments, in one embodiment as illustrated in FIG. 1, where the absorbent layer 24 is joined to the two fabric layers 22X, 22N, the user puts the undergarment 10 on the child. When the child urinates in the undergarment 10, he or she experiences the sensation of wetness to learn to connect the urge to urinate and urinating connected to the discomfort of wetness. The undergarment 10 is removed from the child. If the undergarment 10 is disposable, it is discarded. If the undergarment 10 is washable, the user launders it.

In another embodiment, where the two fabric layers 22X, 22N are joined at the waistband 14, as illustrated in FIG. 4, the user turns the inner fabric underwear 20N inside out, placing the absorbent insert 52 on the crotch 30 of the inside surface of the outer fabric underwear 29X and turning the inner fabric underwear 20N right side in. The user puts the undergarment 10 on the child. If the child urinates in the undergarment 10 or when the undergarment 10 is ready to be laundered, the user removes the undergarment 10 from the child, turns the inner fabric underwear 20N inside out, removes and discards the absorbent insert 52 and launders the undergarment 10.

In other embodiments, where the undergarment has a channel 40 for an absorbent panel 50, such as illustrated in FIG. 1 and FIG. 5, the user inserts the panel 50 into the channel 40 prior to putting the undergarment 10 on the child. If the absorbent panel 50 has a barrier layer, the barrier layer is placed facing the outer fabric layer. The user puts the undergarment 10 on the child. If the child urinates in the undergarment 10 or when the undergarment 10 is ready to be laundered, the user removes the undergarment 10 from the child, pulls and discards the absorbent panel 40 from the channel and launders the undergarment 10.

Figure 6:
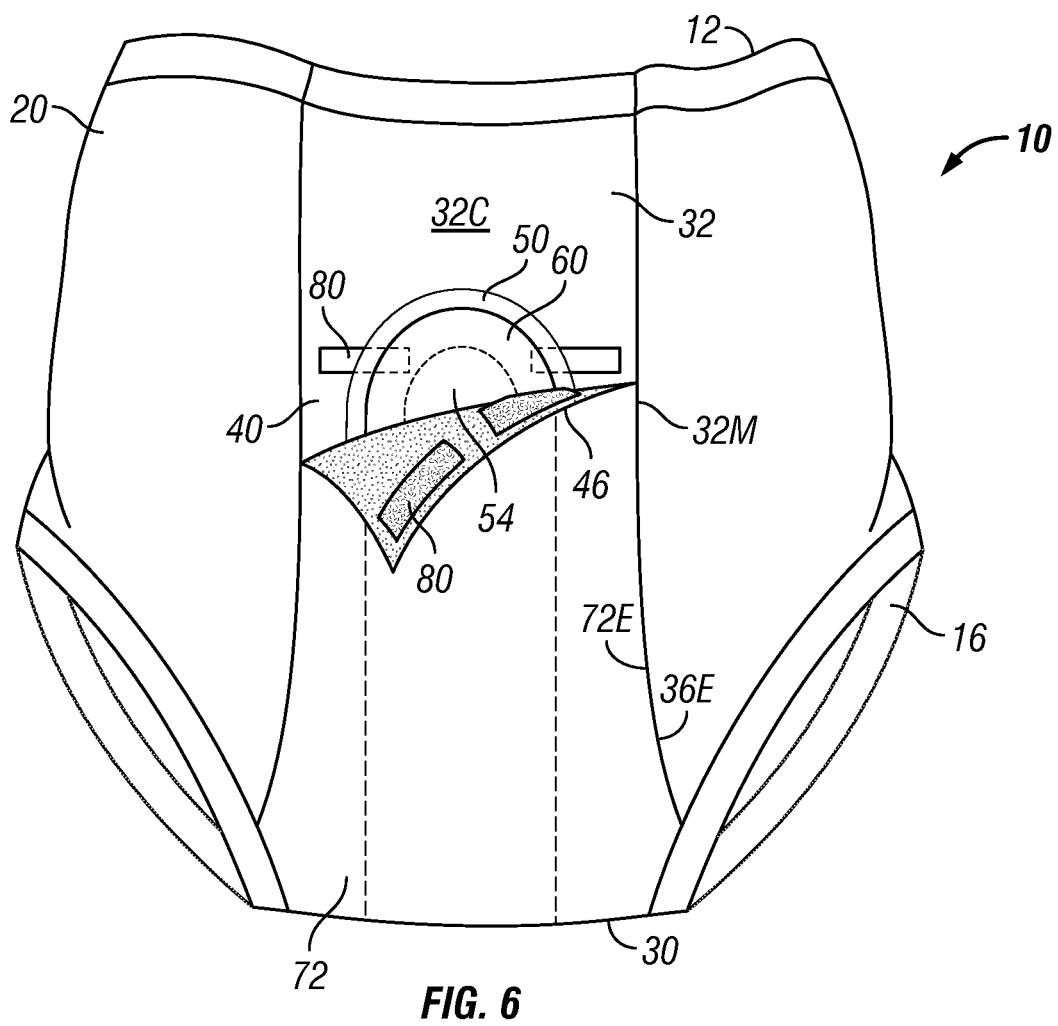
FIG. 6 is a diagrammatic perspective view of a fabric underwear from the front with a truncated channel and the absorbent panel therein.

FIG. 6 shows a further embodiment of the multiple-layer undergarment 10. The first layer, the inner fabric layer is a complete underwear garment 20, having a waist opening 12, a pair of leg openings 16, a crotch 30 between the leg openings, a front segment 32 and a back segment 34, each extending from the crotch 30 to the waist opening 12 forming a center panel 32C having a pair of longitudinal side edges 32E, the center panel 32C having a front middle portion 32M and rear middle portion 34M between the crotch and the waist opening, a pair of side segments 36 having a pair of edges 36E, the longitudinal side edges of the center panel joining the edges of the side segments.

A second layer, an outer panel 72 is joined to the center panel 32C at the longitudinal sides 32E, the outer panel extending from the front middle portion 32M of the center panel to the rear middle portion 34M (shown in FIG. 7) of the center panel 32C, the outer panel forming a truncated channel 40 with the center panel of the inner fabric layer 20, the channel for selectively maintaining an absorbent panel 50 for absorbing urine when the child urinates.

Figure 7:
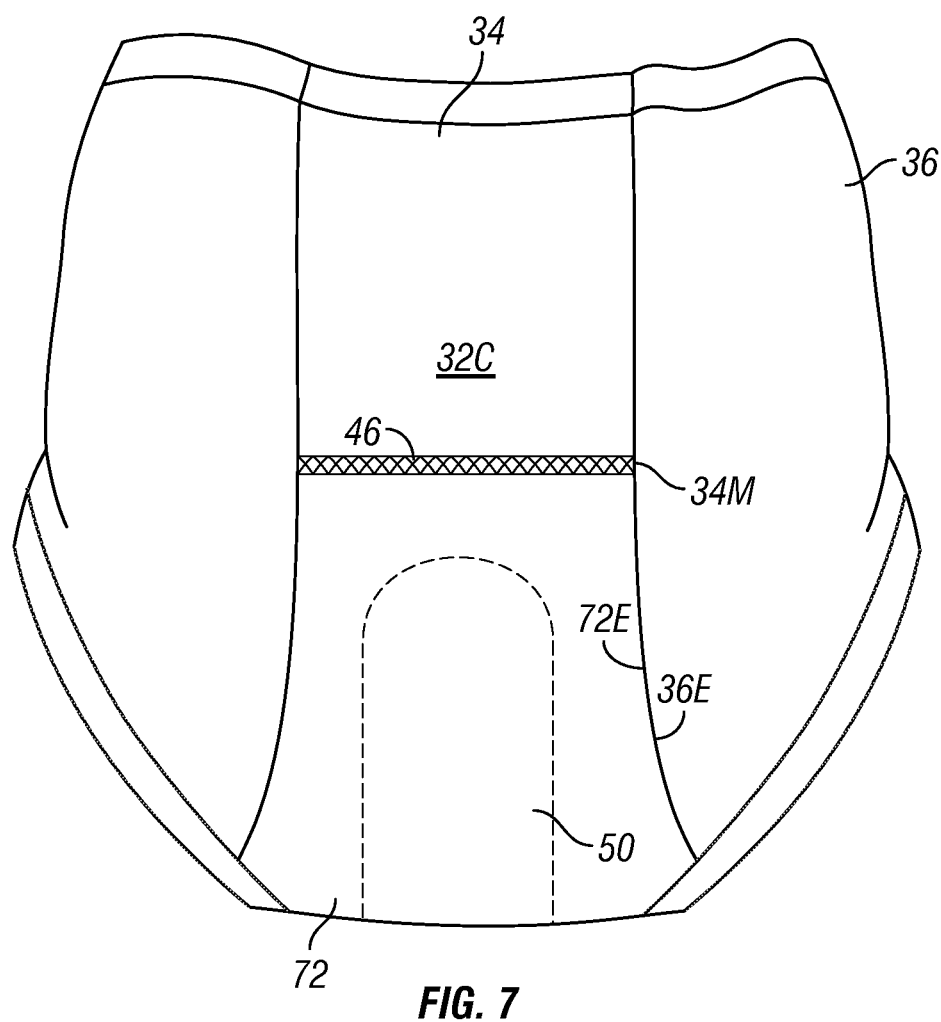
FIG. 7 is a diagrammatic perspective view of the fabric underwear from the rear with the truncated channel closed and the absorbent panel therein.

Referring to FIG. 7, in one embodiment, the channel has a pair of ends 46, a first end and a second end, and the first end of the channel is attached to the center panel 32C, closing the first end of the channel. As illustrated, the first end 46 attaches at the rear middle portion 34M, the second end 46 at the front middle portion remaining selectively open. However, it is understood that the first end attaching to the front middle portion and the second end remaining selectively open is possible within the inventive concept. In one embodiment, the outer panel extends beyond the first end of the channel, to the waist, the end of the channel at the rear middle portion closed to prevent the absorbent layer from moving away from the crotch. In another embodiment, the outer panel extends to the rear middle portion. In yet a further embodiment, both ends of the channel are selectively open.

In the drawing as a non-limiting example, the second end of the channel is selectively closed by a plurality of hook and look fasteners 80. The second end of the channel is selectively closed by fasteners, such as for example, by not limited to, hook and loop fasteners, snaps and buttons.

In the channel 40, the absorbent panel 50 is maintained adjacent to the inner fabric layer 20. In one embodiment, the panel has a moisture barrier layer 60 maintained adjacent to the outer panel 72.

Figure 8:
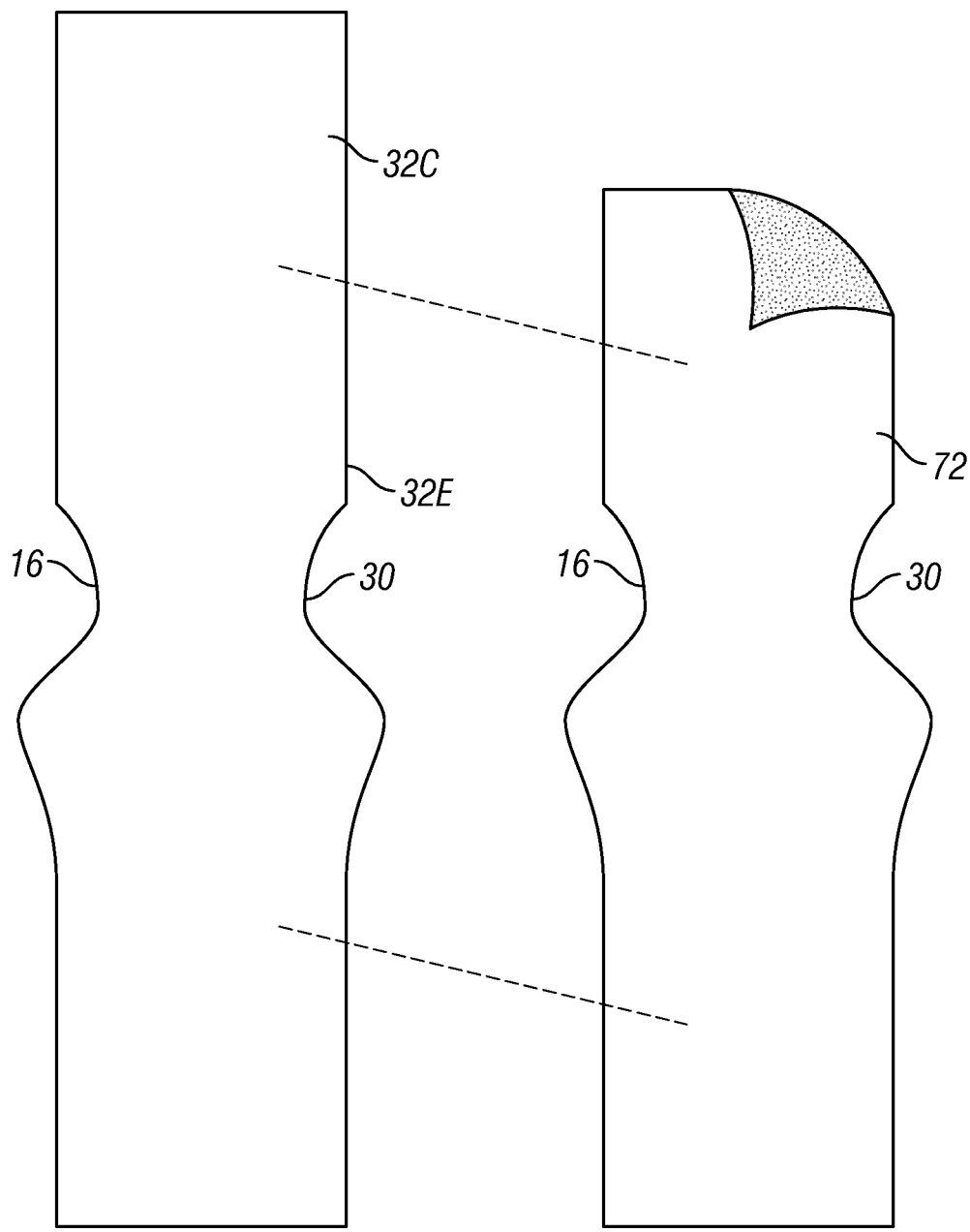
FIG. 8 is a top plan view of a pair of fabric sections forming the channel.

FIG. 8 shows the outer panel 72 and the center panel 32C. The outer panel and center panel form the leg openings 16. The outer panel conforms to the center panel for ease in manufacturing so that the outer panel is joined to the center panel to form the channel and then attached to the sides to form the final multi-layer undergarment.

The outer panel 72 is one embodiment is fabric. In a further embodiment the outer panel is a moisture barrier.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a multiple-layer undergarment to aid toilet training that provides the child with a sensation of wetness, but protects the child's outer garments from being saturated. The disclosure is illustrated by example in the drawing figures, and throughout the written description. It should be understood that numerous variations are possible, while adhering to the inventive concept. Such variations are contemplated as being a part of the present disclosure.

What is claimed is:
1. An undergarment comprising:
a waist band, a left side panel, a right side panel, a center panel comprising a crotch region and two longitudinal sides, an inner fabric layer, and an absorbent pad,
wherein the left side panel, right side panel, and each of the longitudinal sides of the center panel are attached to the waist band, the left side panel is attached to the center panel which together define a first leg opening, and the right side panel is attached to the center panel which together define a second leg opening, and,
wherein the inner fabric layer is attached to the inner surface of the center panel forming a channel that is substantially perpendicular to the longitudinal sides and extends through the crotch region, and wherein the inner fabric layer comprises a material that retains wetness, and wherein the absorbent pad is disposed within the channel formed between the center panel and the inner fabric layer.

2. The undergarment of claim 1, wherein the absorbent pad further comprises a moisture barrier layer between an absorbent material and the outer fabric layer.

3. The undergarment of claim 1, wherein the channel extents from the first longitudinal side of center panel to the second longitudinal side of the center panel.

4. The undergarment of claim 1, wherein the channel extends from a front middle portion of the center panel to a back middle portion of the center panel.

5. The undergarment of claim 1, wherein the channel is open at both ends.

6. The undergarment of claim 1, wherein the channel further comprises at least one reversible closure at an end.

7. The undergarment of claim 6, wherein reversible closure comprises hook and loop fasteners.

8. An undergarment comprising:
a waist band, a left side panel, a right side panel, a center panel comprising a crotch region and two longitudinal sides, an outer fabric layer, and an absorbent pad, wherein the left side panel, right side panel, and each of the longitudinal sides of the center panel are attached to the waist band, the left side panel is attached to the center panel which together define a first leg opening, and the right side panel is attached to the center panel which together define a second leg opening, and, wherein the outer fabric layer is attached to the outer surface of the center panel forming a channel that is substantially perpendicular to the longitudinal sides and extends through the crotch region, and wherein the center panel comprises a material that retains wetness, and wherein the absorbent pad is disposed within the channel formed between the center panel and the outer fabric layer.

9. The undergarment of claim 8, wherein the absorbent pad further comprises a moisture barrier layer between an absorbent material and the outer fabric layer.

10. The undergarment of claim 8, wherein the channel extents from the first longitudinal side of center panel to the second longitudinal side of the center panel.

11. The undergarment of claim 8, wherein the channel extends from a front middle portion of the center panel to a back middle portion of the center panel.

12. The undergarment of claim 8, wherein the channel is open at both ends.

13. The undergarment of claim 8, wherein the channel further comprises at least one reversible closure at an end.

14. The undergarment of claim 13, wherein reversible closure comprises hook and loop fasteners.

* * * * *